United States Patent [19]
Guzaev et al.

[11] Patent Number: 5,959,090
[45] Date of Patent: Sep. 28, 1999

[54] CHEMICAL PHOSPHORYLATION OF OLIGONUCLEOTIDES AND REACTANTS USED THEREFOR

[75] Inventors: Andrei Guzaev, Carlsbad, Calif.; Alex Azhayev, Kuopio; Harri Lonnberg, Turku, both of Finland

[73] Assignee: Glen Research Corporation, Sterling, Va.

[21] Appl. No.: 08/886,456

[22] Filed: Jul. 1, 1997

Related U.S. Application Data

[60] Provisional application No. 60/021,099, Jul. 2, 1996, abandoned.

[51] Int. Cl.[6] .............................. C12Q 1/68; C07H 19/00; C07H 21/02; C07H 21/00
[52] U.S. Cl. ..................... 536/23.1; 435/6; 536/22.1; 536/25.3; 536/25.31; 536/25.33; 536/25.34
[58] Field of Search ................. 536/22.1, 25.3, 536/25.31, 25.33, 25.34, 23.1; 435/6

[56] References Cited

U.S. PATENT DOCUMENTS

| | | | |
|---|---|---|---|
| 5,252,760 | 10/1993 | Urdea et al. | 552/105 |
| 5,332,845 | 7/1994 | Urdea et al. | 552/105 |

FOREIGN PATENT DOCUMENTS

| | | |
|---|---|---|
| 0272007 | 6/1988 | European Pat. Off. . |
| 0304215 | 2/1989 | European Pat. Off. . |
| WO92/06103 | 4/1992 | WIPO . |

OTHER PUBLICATIONS

Guzaev, et al., "A New Approach for Chemical Phosphorylation of Oligonucleotides at the 5′–Terminus," *Tetrahedron*, vol. 51, No. 34 (1995), pp. 9375–9384.

Modrich et al., "Deoxyribonucleic Acid Ligase," *The Journal of Biological Chemistry*, vol. 248, No. 21 (1973), pp. 7502–7511.

Fritz, "The Oligonucleotide–directed Construction of Mutations in Recombinant Filamentous Phage," Chapter 8, *DNA Cloning: A Practical Approach*, vol. I, IRL Press, Oxford, 1985, pp. 151–163.

Barany, "The Ligase Chain Reaction in a PCR World," *PCR Methods and Applications*, vol. I (1991), pp. 5–16.

Bannwarth et al. "A New Combined Purification/Phosphorylation Procedure for Oligodeoxynucleotides," *Helvetica Chimica Acta*, vol., 73 (1990), pp. 1139–1147.

(List continued on next page.)

*Primary Examiner*—Ardin H. Marschel
*Assistant Examiner*—Jezia Riley
*Attorney, Agent, or Firm*—Finnegan, Henderson, Farabow, Garrett & Dunner, L.L.P.

[57] ABSTRACT

Phosphoramidite building blocks according to the following formula 1 are used for phosphorylating oligonucleotides, preferably at the 5′- or 3′-terminus. The building blocks include phosphoramidite compounds according to formula 1:

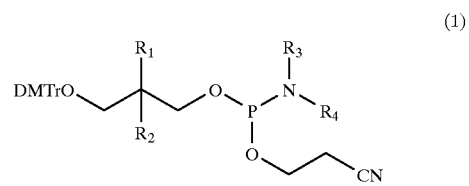

(1)

wherein DMTr is a 4,4′-dimethoxytrityl group; $R_1$ is an electron withdrawing group; $R_2$ is an electron withdrawing group which may be the same or different from the $R_1$ group; $R_3$ is an alkyl group; and $R_4$ is an alkyl group which may be the same or different from the $R_3$ group. Preferred electron withdrawing groups include —$CO_2Et$ groups, —$CO_2Me$ groups, —CN groups, —$CON(Me)_2$ groups, and —CONHMe groups, wherein Et represents an ethyl group and Me represents a methyl group. One preferred alkyl group is an isopropyl group.

40 Claims, 2 Drawing Sheets

RP HPLC PROFILE OF CRUDE 13.

OTHER PUBLICATIONS

Gorn et al., "Synthesis of 5'–Phosphorylated Oligodeoxyribonucleotides by Phosphotriester Solid Phase Method in Manual and Automated Variants," *Bioorg. Khim. (Moscow)*, vol. 12, No. 8 (1986), pp. 1054–1063.

Gaffney et al. "Large–Scale Oligonucleotide Synthesis by the H–Phosphonate Method," *Tetrahedron Letters*, vol. 29, No. 22 (1988), pp. 2619–2622.

Marsters et al. "5'–Phosphorylation of Oligonucleotides with Phosphorous Acid in Automated DNA Synthesis," *Nucleosides & Nucleotides*, vol. 9, No. 8 (1990), pp. 1079–1086.

Horn et al., "A Chemical 5'–Phosphorylation of Oligodeoxyribonucleotides," *DNA*, vol. 5, No. 5 (1986), pp. 421–426.

Wosnick et al., "Rapid Construction of Large Synthetic Genes: Total Chemical Synthesis of Two Different Versions of the Bovine Prochymosin Gene," *Gene*, vol. 60 (1987), pp. 115–127.

Robertson et al., "The Use of 5'–Phospho–2 Deoxyribocytidylylriboadenosine as a Facile Route to Chemical Aminoacylation of tRNA," *Nucleic Acids Research*, vol. 17, No. 23 (1989), pp. 9649–9660.

Horn et al., "A Chemical 5–Phosphorylation of Oligodeoxyribonucleotides that can be Monitored by Trityl Cation Release," *Tetrahedron Letters*, vol. 27, No. 39 (1986), pp. 4705–4708.

Coe et al., "An Improved Method for the Synthesis of Highly Substituted Alkyl Phosphates Including Nucleoside 5'–Phosphates," *Chemistry & Industry*, No. 21 (1989), pp. 724–725.

Sekine et al., "A Convenient Method for Removal of the t–Butyl Group from Nucleoside Bis(t–Butyl) Phosphates under Non–acidic Conditions," *Tetrahedron Letters*, vol. 32, No. 3 (1991), pp. 395–398.

Uhlmann et al., "Chemical 5'–Phosphorylation of Oligonucleotides Valuable in Automated DNA Synthesis," *Tetrahedron Letters*, vol. 27, No. 9 (1986), pp. 1023–1026.

Uhlmann et al., "Automated 5'–Phosphorylation of Oligodeoxyribonucleotides," *Chemica Scripta*, vol. 26 (1986), pp. 217–219.

Schwarz et al., "Synthesis of Terminal Nucleoside Phosphates and Thiophosphates via Phosphoramidite Chemistry," *Nucleosides & Nucleotides*, vol. 6, Nos. 1 and 2 (1987), pp. 537–539.

Bower et al., "Synthesis and Characterization of Oligodeoxyribonucleotides Containing Terminal Phosphates," *Nucleic Acids Research*, vol. 15, No. 8 (1987), pp. 3531–3547.

Connolly et al., "Chemical Synthesis of Oligonucleotides Containing a Free Sulphydryl Group and Subsequent Attachment of Thiol Specific Probes," *Nucleic Acids Research*, vol. 13, No. 12 (1985), pp. 4485–4502.

Connolly, "Solid Phase 5'–Phosphorylation of Oligonucleotides," *Tetrahedron Letters*, vol. 28, No. 4 (1987), pp. 463–466.

Celebuski et al., "Synthesis and Utility of a DNA Phosphorylating Agent Based on 2–(Triphenylsilyl)ethanol," *Journal of Organic Chemistry*, vol. 57, No. 20 (1992), pp. 5535–5538.

Block, Jr., "Diethyl Bis(hydroxymethyl)malonate," *Organic Syntheses*, vol. 40 (1960), pp. 27–28.

Nielsen et al., "Improved Synthesis of $(Pr_2^i N)_2POCH_2CH_2CN$," *Nucleic Acids Research*, vol. 15, No. 8 (1987), p. 3626.

Hovinen et al., Novel Solid Supports for the Preparation of 3'–Derivatized Oligonucleotides: Introduction of 3'–Alkylphosphate Tether Groups Bearing Amino, Carboxy, Carboxamido, and Mercapto Functionalities, *Tetrahedron*, vol. 50, No. 24 (1994) pp. 7203–7218.

Ramalingam et al., "Synthesis of Nitroimidazole Substituted 3,3,9,9–Tetramethyl–4,8–diaza–undecane–2,10–dione Dioximes (Propylene Amine Oximes, PnAOs): Ligands for Technetium–99m Complexes with Potential for Imaging Hypoxic Tissue," *Tetrahedron*, vol. 51, No. 10 (1995), pp. 2875–2894.

MacCorquodale et al., "Cycloalkylmethyl Radicals. Part 8. A Conformational Study of Dioxa– and Dithia–cyclohexylmethyl Radicals by EPR Spectroscopy," *Journal of the Chemical Society: Perkin Transactions 2*, No. 12 (1991), pp. 1893–1899.

Hughes et al., "Cycloalkylmethyl Radicals. 6. The Unexpectedly High Barrier to the Rotation of Axial $CH_2$ Groups in Cyclohexylmethyl Radicals," *Journal of the American Chemical Society*, vol. 110, No. 22 (1988), pp. 7494–7499.

Bosies et al., "Synthesis of Thioether Phosphocholine Analogues," *Lipids*, vol. 22, No. 11 (1987), pp. 947–951.

Teuber et al., "Synthesis and Thermal Stability of 4–Substituted 1,2–Dithiolanes," *Acta Chemica Scandinavica*, vol. B42 (1988), pp. 629–634.

March, "Advanced Organic Chemistry–Reactions, Mechanisms, and Structure, "J. Wiley & Sons, N.Y., 3rd Ed., 1985, pp. 689–691 and 829–834.

Casy et al., "Mechanism of a Mannich Base Exchange Reaction," *Journal of the Chemical Society*, (1964), pp. 4639–4640.

Yanagawa et al., "A Convenient Procedure for the Synthesis of Asparagusic Acids," *Synthesis*, No. 10 (1973), pp. 607–608.

Cassady et al., "Methyl α–(Bromomethyl)acrylate," *Organic Syntheses*, vol. 61 (1983), pp. 77–82.

Haynes et al., "Preparation of t–Butyl 2–(Phenylthiomethyl)propenoate, t–Butyl 3–(Phenylthio)–2–(phenylthiomethyl)propenoate and Related Compounds," *Australian Journal of Chemistry*, vol. 37, No. 7, pp. 1571–1578, (1984).

Singh et al., "Comparisons of Rate Constants for Thiolate–Disulfide Interchange in Water and in Polar Aprotic Solvents Using Dynamic $^{1}H$ NMR Line Shape Analysis," *Journal of the American Chemical Society*, vol. 112, No. 3, pp. 1190–1197, 1990.

Guzaev, et al., "Synthesis of Oligonucleotide Analogs by using Phosphoramidite Reagents Derived from 2,2–bis(hydroxymethyl)malonates," *Chemical Abstracts*, vol. 125, No. 25 (1996), Abstract No. 125:329248c.

Tanaka et al., "An Intermediate for the Synthesis of 5'–Phosphorylated Oligodeoxyribonucleotides," *Nucleic Acid Chem.*, Section IV, Nucleotides and Polynucleotides, Wiley, N.Y., 1991, pp. 314–319.

Conant et al., "Diacetone Alcohol," *Organic Synthesis*, Collective vol. 1, pp. 199–201, 1941.

RP HPLC PROFILE OF CRUDE 14.

ION EXCHANGE PROFILE OF CRUDE 11b.

SEQUENCE LISTING

<160> NUMBER OF SEQ ID NOS: 1

<210> SEQ ID NO 1
<211> LENGTH: 15
<212> TYPE: DNA
<213> ORGANISM: Rattus rattus

<400> SEQUENCE: 1
gaacatcatg gtcgt                15

CHEMICAL PHOSPHORYLATION OF OLIGONUCLEOTIDES AND REACTANTS USED THEREFOR

RELATED APPLICATION DATA

This application claims priority benefits under 35 U.S.C. § 119 and any other applicable statutes or regulations based on U.S. Provisional Patent Appl. No. 60/021,099, filed Jul. 2, 1996, which application is entirely incorporated herein by reference.

BACKGROUND OF THE INVENTION

Oligonucleotides possessing 5'-phosphate groups are useful for many purposes. For example, these oligonucleotides are valuable tools for gene construction (Modrich et al., *J Biol. Chem.*, 1973, 248, 7502–7511); cloning (Sambrook et al., *Molecular Cloning: A Laboratory Manual*, 1989, Cold Spring Harbor Press, Cold Spring Harbor, N.Y.); mutagenesis (Fritz, *DNA Cloning: A Practical Approach*, IRL Press, Oxford, 1985, 1, 151–163); the ligation chain reaction (Barany, *PCR Methods and Applications*, 1991, I, 5–16); and many other biological applications. The above-noted documents each are entirely incorporated herein by reference. Often, such oligonucleotides are prepared by T4 kinase catalyzed phosphorylation employing adenosine 5'-triphosphate as a phosphate source (Sambrook et al., supra.).

A number of methods have been reported that allow chemical 5'-phosphorylation of pre-assembled oligonucleotide precursors. Some of them include preparation of modified nucleoside-based building blocks to be attached at the last step of the oligonucleotide synthesis (Bannwarth et al., *Helv. Chim. Acta*, 1990, 73, 1139–1147; and Tanaka et al., *Nucleic Acid Chem.*, Wiley: N.Y., 1991, 4, 314–319; each of these documents is entirely incorporated herein by reference). Another strategy, based on non-nucleosidic building blocks, seems to be more universal, because a single reagent may be employed. A variety of approaches compatible with phosphotriester (Gorn et al., *Bioorg. Khim. (Moscow)*, 1986, 12, 1054–1063), H-phosphonate (Gaffney et al., *Tetrahedron Lett.*, 1988, 29, 2619–2622; and Marsters et al., *Nucleosides Nucleotides*, 1990, 9, 1079–1086), methyl phosphonamidite (Bhan, *Tetrahedron Lett.*, 1944, 35, 4905–4898), or phosphoramidite (Horn et al., *DNA*, 1986, 5, 421–426; Wosnick et al., *Gene*, 1987, 60, 115–127; and Robertson et al., Nucleic Acids Res., 1989, 17, 9649–9660) chemistry have been elaborated. Each of the above-noted documents is entirely incorporated herein by reference.

All of these approaches suffer from the same shortcoming: the efficiency of the final coupling cannot be monitored by dimethoxytrityl response. In order to overcome this problem, a building block derived from (4,4'-dimethoxytrityloxyethyl) hydroxyethyl sulfone has been introduced (Horn et al., *Tetrahedron Letters*, 1986, 27, 4705–4708, which article is entirely incorporated herein by reference). See also U.S. Pat. No. 5,252,760, which patent is entirely incorporated herein by reference. Upon completion of the final chain elongation step, the 5'-derivatized oligonucleotide possesses a 5'-terminal tether containing a dimethoxytrityl protecting group. This group can be used to determine the coupling yield by conventional dimethoxytrityl assay. Ammonolytic deprotection, however, results in β-elimination of the O-phosphorylated hydroxyethyl sulfone fragment, and hence the dimethoxytrityl group is lost on release of the 5'-phosphate group. Accordingly, performing dimethoxytrityl specific isolation of the oligonucleotide is excluded.

It is well known that preparative reverse phase ("RP") separation of oligonucleotide 5'-phosphates from the corresponding non-phosphorylated material is often unsuccessful. The use of more efficient ion exchange chromatography is, in turn, restricted by the length of the DNA fragment to be isolated. Therefore, approaches that offer a selective isolation of the desired oligonucleotide remain to be of particular interest.

A family of methods, all involving an "orthogonal" protection strategy of the 5'-terminal phosphate, has been elaborated. After the chain assembly and ammonolytic deblocking, the orthogonal protection of the 5'-phosphate [t-butyl (Coe et al., *Chem. Ind*, 1989, 724–725; and Sekine et al., *Tetrahedron Lett.*, 1991, 32, 395–398.), (4-nitrophenyl)ethyl (Uhlmann et al., *Tetrahedron Lett.*, 1986, 27, 1023–1026; Uhlmann et al., *J Chem. Scr.*, 1986, 26, 217–219; Schwarz et al., *Nucleosides Nucleotides*, 1987, 6, 537–539; and Bower et al., *Nucleic Acids Res.*, 1987, 15, 3531–3547), 2-(tritylthio)ethyl (Connolly et al., *Nucleic Acids Res.*, 1985, 13, 4485–4502; and Connolly, *Tetrahedron Lett.*, 1987, 28, 463–466), or 2-(triphenylsilyl)ethyl (Celebusky et al., *J Org. Chem.*, 1992, 57, 5535–5538)] remains unchanged. These documents also are each entirely incorporated herein by reference. Being of moderate hydrophobicity, the t-butyl and (4-nitrophenyl)ethyl protecting groups enable efficient separation only for relatively short oligonucleotides. In contrast, the 2-(tritylthio)ethyl or 2-(triphenylsilyl)ethyl groups are more hydrophobic than the dimethoxytrityl group, and hence the desired oligonucleotides may be very selectively isolated by reverse phase, high performance liquid chromatography ("RP HPLC") or reverse phase cartridge purification. After the purification, free 5'-phosphate monoester is released by treatment with an appropriate reagent, such as trifluoroacetic acid or trimethylsilyl chloride for t-Bu; strong amine (DBU, TBD, and others) for (4-nitrophenyl)ethyl; or 2 M $Bu_4NF$/DMSO at 70° C. for 2-(triphenylsilyl)ethyl. In this respect, the 2-(tritylthio)ethyl group offers the mildest deprotection technique. To obtain the 5'-phosphate, the trityl-S bond was selectively cleaved by aqueous silver nitrate or iodine. Subsequent addition of dithiothreitol at pH 8.5 generates in both cases mercaptide ion which rapidly degrades to the target oligonucleotide 5' phosphate and ethylene sulfide.

There is a need in the art for reagents and an efficient process for producing high purity phosphorylated oligonucleotides. Preferably, this method would use reagents that are commonly available and used in DNA synthesis.

SUMMARY OF THE INVENTION

It is one object of this invention to provide reagents and a method for chemical phosphorylation of oligonucleotides. The invention includes phosphoramidite building blocks according to the following formula 1, which materials can be used, for example, for phosphorylating oligonucleotides at the 5'- or 3'-terminus. Suitable compounds according to the invention include phosphoramidite compounds according to formula 1

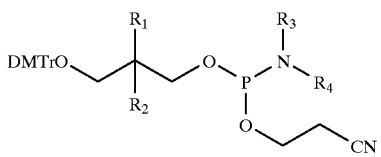

(1)

wherein DMTr is a 4,4'-dimethoxytrityl group; $R_1$ is an electron withdrawing group; $R_2$ is an electron withdrawing group which may be the same or different from the $R_1$ group; $R_3$ is an alkyl group; and $R_4$ is an alkyl group which may be the same or different from the $R_3$ group. The term "alkyl group," as used in this application, means a straight or branched organic moiety having 1 to 10 carbon atoms. Preferably, the alkyl group will have between 1 and 5 carbon atoms. Isopropyl moieties are particularly preferred alkyl groups for $R_3$ and $R_4$.

$R_1$ and $R_2$ can be the same or different moiety, and can be any suitable electron withdrawing group. Preferably, $R_1$ and $R_2$ each are independently a member selected from the group consisting of an amide group or an ester group. Particularly preferred electron withdrawing groups include —$CO_2Et$ groups, —$CO_2Me$ groups, —CN groups, —$CON(Me)_2$ groups, and —CONHMe groups, wherein Et represents an ethyl group and Me represents a methyl group.

Specific phosphoramidite building blocks according to the invention include phosphoramidites having the following structures:

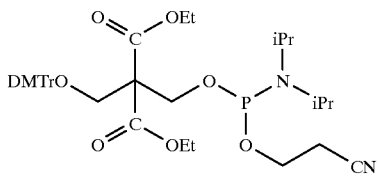

wherein Et is an ethyl group and iPr is an isopropyl group;

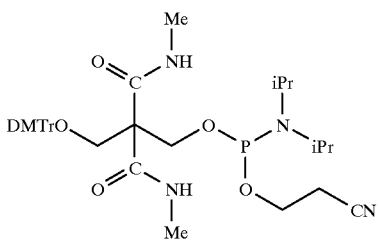

wherein Me is a methyl group and iPr is an isopropyl group; and

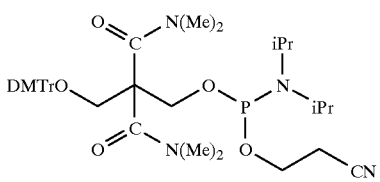

wherein Me is a methyl group and iPr is an isopropyl group.

The invention further relates to a process for preparing substantially pure oligonucleotides having a phosphate group at the 3'- or 5'-terminus. The term "substantially pure," in this art, is a relative term, depending on various factors, such as the oligonucleotide chain length. The process of the invention can be used to make oligonucleotides of high purity, such as 75% pure or higher. Preferably, the product purity is 80%, 90%, or even 95% or higher using the process of the invention.

The process of the invention includes reacting a support-bound 4,4'-dimethoxytrityl protected oligonucleotide of the formula:

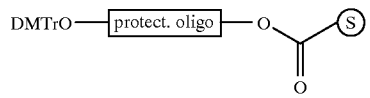

wherein DMTr is 4,4'-dimethoxytrityl group and S is a support material, with a phosphoramidite of formula 1:

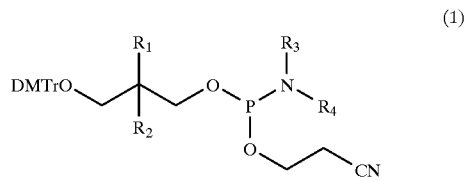

(1)

wherein DMTr is a 4,4'-dimethoxytrityl group; $R_1$ is an electron withdrawing group; $R_2$ is an electron withdrawing group which may be the same or different from the $R_1$ group; $R_3$ is an alkyl group; and $R_4$ is an alkyl group which may be the same or different from the $R_3$ group, to form a phosphorylated oligonucleotide of the formula:

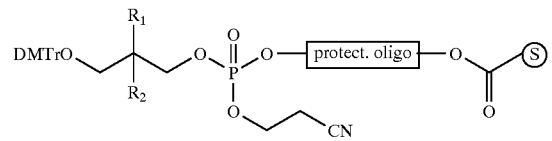

Phosphoramidite materials such as those described above can be used in this phosphorylation reaction. After phosphorylation, the phosphorylated oligonucleotide is cleaved from the support material to provide an unbound phosphorylated oligonucleotide of the formula:

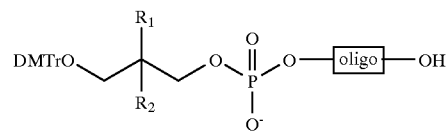

This material is recovered, the DMTr group is removed to form a phosphorylated oligonucleotide of the formula:

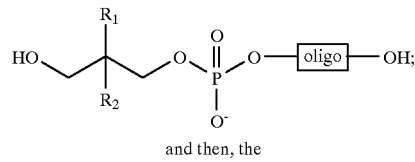

and then, the

-continued

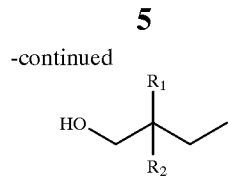

side chain on the phosphorylated oligonucleotide is removed to provide an oligonucleotide having a phosphate group at the 5'-terminus of the formula:

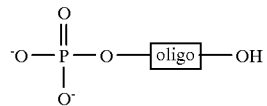

The unbound phosphorylated oligonucleotide shown above can be recovered by any suitable process known to those in the art. For example, a reverse phase separation technique, such as reverse phase, high performance liquid chromatography, can be used to recover the unbound phosphorylated oligonucleotide.

Any suitable support material that is known in the art, such as those disclosed in U.S. Pat. No. 5,252,760, can be used to support the oligonucleotide starting material without departing from the invention. Examples of suitable support materials include silica, controlled pore glass, long chain alkyl amino controlled pore glass, and polystyrene. In addition, any suitable oligonucleotide can be phosphorylated according to the process of the invention. Suitable oligonucleotides include oligonucleotides having a nucleotide chain with from about 2 to about 200 component nucleotide monomers, preferably from about 2 to about 100 monomers.

BRIEF DESCRIPTION OF THE DRAWINGS

The advantageous features of the invention will be more fully appreciated when considered based on the following detailed description and the attached drawings, wherein.

DETAILED DESCRIPTION OF THE INVENTION

Figure 1:
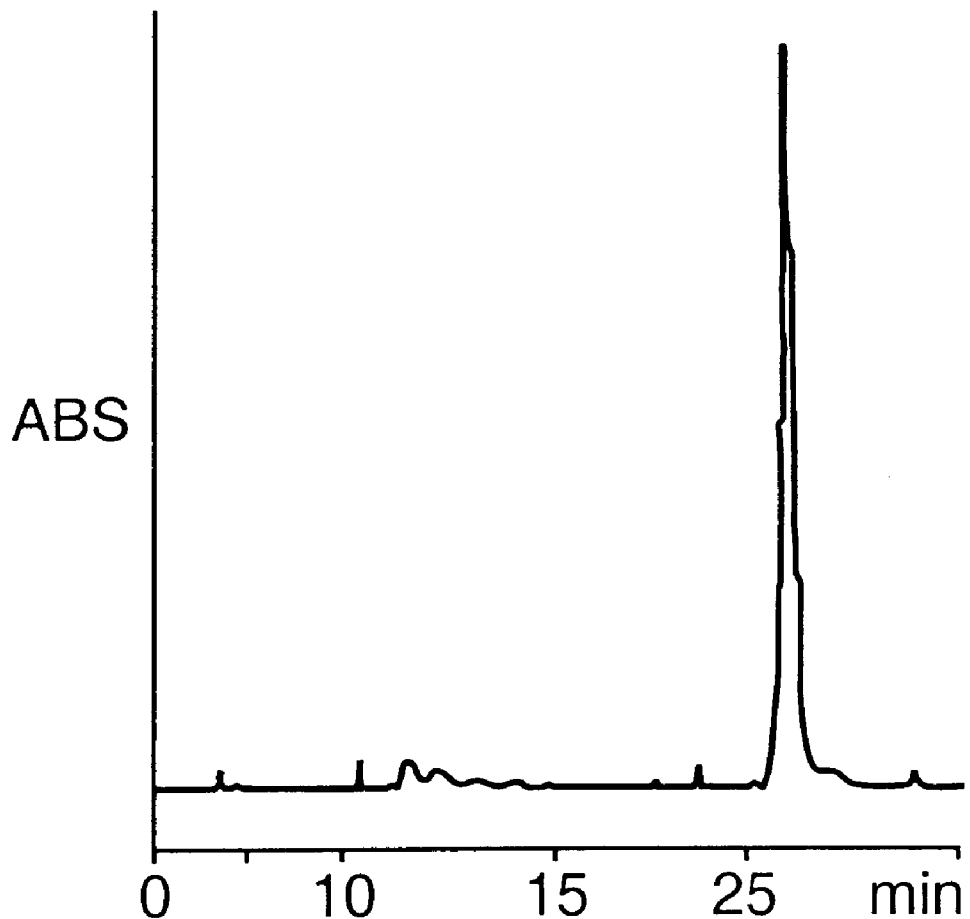
FIG. 1 is an RP HPLC profile of compound 13 in its crude form.

This invention relates to a new approach for preparing phosphorylated oligonucleotides using phosphoramidite building blocks according to the invention. Oligonucleotides phosphorylated at the 3'- or 5'-terminus can be produced using the building blocks according to the invention. The building blocks of the invention include phosphoramidite compounds of formula 1:

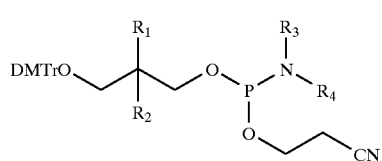

wherein DMTr is a 4,4'-dimethoxytrityl group; $R_1$ and $R_2$ are electron withdrawing groups (such as amides and esters);

and $R_3$ and $R_4$ are alkyl groups. Suitable electron withdrawing groups include —$CO_2Et$ groups, —$CO_2Me$ groups, —CN groups, —$CON(Me)_2$ groups, and —CONHMe groups, wherein "Me" is a methyl substituent and "Et" is an ethyl substituent. Various alkyl groups, as described above, can be used as the $R_3$ and $R_4$ groups according to the invention. One suitable alkyl group is an isopropyl group.

The compounds according to the invention are not limited to those illustrated in formula 1. For example, while the 4,4'-dimethoxytrityl group (DMTr) is preferred, other suitable substituent groups can replace the DMTr group. This DMTr group can be replaced, for example, by any of the substituent groups described by variable "$R_1$" in U.S. Pat. No. 5,252,760. Likewise, the variables $R_3$ and $R_4$ in formula 1 can be defined in the same manner as variables "$T^1$" and "$T^2$" in U.S. Pat. No. 5,252,760. Additionally, the "—$CH_2CH_2CN$" group shown in formula 1 can be replaced by the substituents described as variable "D" in U.S. Pat. No. 5,252,760. U.S. Pat. No. 5,252,760, including the definitions of $R_1$, $T^1$, $T^2$, and D, is entirely incorporated herein by reference.

The invention further relates to a method for phosphorylating an oligonucleotide using the building blocks of the invention. For 5'-terminus phosphorylation, a 4,4'-dimethoxytrityl protected oligonucleotide on a support is reacted with the phosphoramidite building block of formula 1 following acid detritylation. After this reaction, ammonolysis produces a DNA fragment selectively protected at the 5'-phosphate group with a dimethoxytritylated tether. At this time, the modified oligonucleotide can be separated easily from truncated impurities by reverse phase HPLC to provide a highly purified oligonucleotide containing product. Successive detritylation and brief treatment with ammonia generates the 5'-phosphate group in more than 98% yield. Thus, the method of the invention is advantageous because it requires only those ancillary reagents that are of daily use in DNA synthesis, but still produces a phosphorylated oligonucleotide product of high purity. As an alternative procedure according to the invention, the product of the last coupling can be quantified by detritylation of the oligonucleotide still anchored to the solid support. Deprotection in this case leads directly to the target 5'-phosphorylated DNA fragment.

The phosphoramidite building blocks according to the invention also can be used for phosphorylation at the 3'-terminus. In this procedure, the phosphoramidite building block 1 is introduced as the first addition to a nucleoside support, followed by normal synthesis of the target oligonucleotide. After synthesis of the target oligonucleotide, standard ammonium hydroxide deprotection decomposes the linkage to the nucleoside support to give the target molecule with a phosphate group at the 3'-terminus. Alternatively, a support of the type

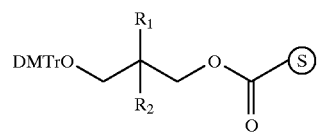

can be prepared directly for a more direct synthesis of 3'-phosphorylated DNA fragments.

The invention now will be described more specifically, with the aid of various reaction schemes and examples. These specific schemes and examples should be construed as illustrating the claimed invention, and not as limiting the same.

The phosphoramidite building blocks according to the invention can be made by any suitable method. The following describes techniques for producing specific phosphoramidites according to the invention. Using the techniques described herein, those skilled in the art will be capable of producing a wide variety of other phosphoramidite building blocks through routine experimentation.

EXAMPLE 1

SCHEME 1(a)

Synthesis of the Phosphoramidite Building Block 1(a)

A first scheme for preparing a phosphoramidite building block according to formula 1 is exemplified in Scheme 1(a). This building block is a di-ester (i.e., it includes ester substituents at $R_1$ and $R_2$).

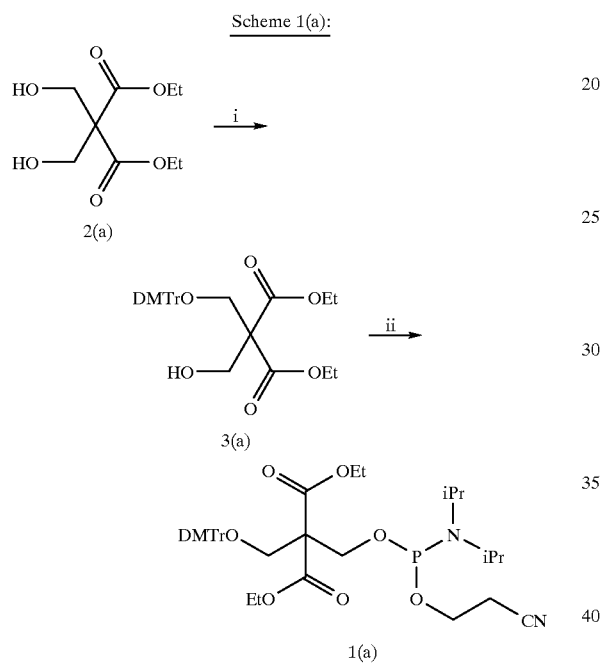

i: a) DMTrCl/Py; b) Et$_3$N/H$_2$O; ii: a) (2-cyanoethyl) N,N,N',N'-tetraisopropylphosphorodiamidite/1H-tetrazole; b) NaHCO$_3$/H$_2$O. DMTr is 4,4'-dimethoxytrityl.

The starting diethyl 2,2-bis(hydroxymethyl)malonate, 2(a), is commercially available. Alternatively, it can be prepared from diethyl malonate in a yield of 75%, as described in Block, Jr., P. Org. Synth., 1960, 40, 27–28; or Coll. Vol. 5, 381–383, which documents each are entirely incorporated herein by reference. One of the hydroxy groups was 4,4'-dimethoxytritylated, and the product, 3(a), was isolated by column chromatography. The DMTr product 3(a) was then converted into phosphoramidite building block 1(a) by treatment with (2-cyanoethyl) N,N,N',N'-tetraisopropylphosphorodiamidite (see Nielsen et al., Nucleic Acids Res., 1987, 15, 3626) in the presence of 1H-tetrazole. This Nielsen article is entirely incorporated herein by reference. After aqueous work-up, compound 1(a) was obtained in a pure form by precipitation from toluene to hexane.

SCHEME 1(b)

Synthesis of the Phosphoramidite Building Block 1(b)

The preparation of a diamine containing phosphoramidite building block of formula 1 is exemplified in this Scheme.

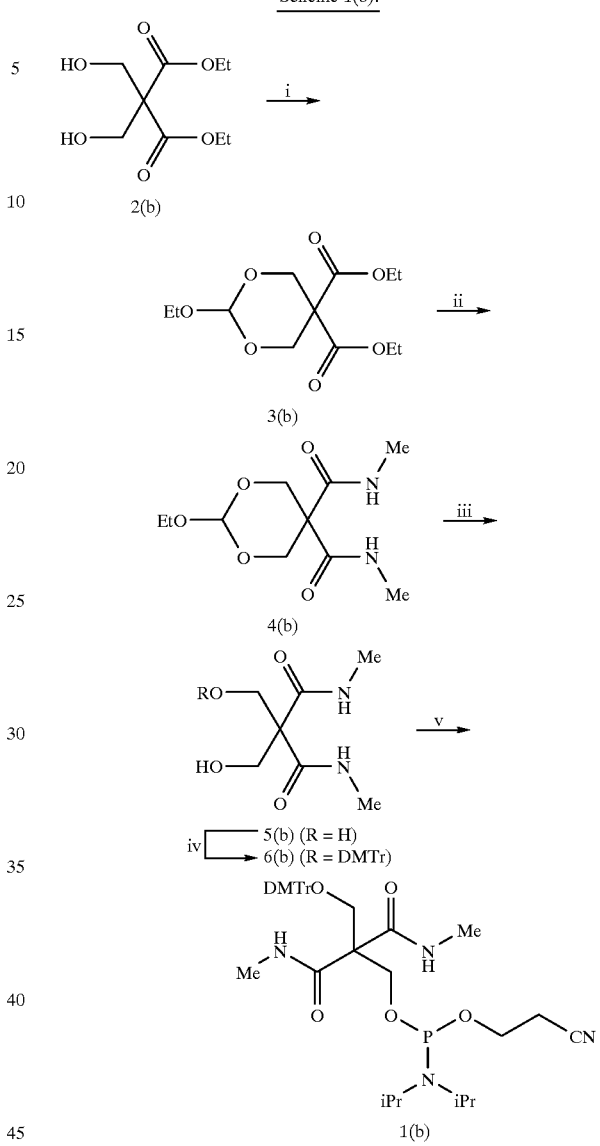

i: (EtO)$_3$CH/H$_2$SO$_4$/dioxane; ii: 40% aqueous methylamine; iii: a) 80% aq. acetic acid; b) 10% triethylamine in MeOH; iv: DMTr-Cl/pyridine; v: 2-cyanoethyl-N,N,N',N'-tetraisopropyl phosphorodiamidite/1H-tetrazole/acetonitrile.

Diethyl 2,2-bis(hydroxymethyl)malonate 2(b), commercially available or provided as described above in Scheme 1(a), was treated as reported previously in Guzaev et al., Biconjugate Chem., 1966, 7, 240–248, which article is entirely incorporated herein by reference, with triethyl orthoformate in dioxane in the presence of a catalytic amount of sulfuric acid to produce compound 3(b). This product 3(b) was isolated by vacuum distillation. Compound 3(b) was reacted with 40% aqueous methylamine at ambient temperature to produce the di(N-methylamide) product, compound 4(b), which was isolated by recrystallization from a mixture of hexane and isopropanol in 70% yield. Compound 4(b) was reacted with 80% aqueous acetic acid followed by treatment with 10% triethylamine in dioxane to give the diol 5(b), which, by reaction with 4,4'-dimethoxytrityl chloride in pyridine, was converted into the mono(4,4'-dimethoxytrityl) derivative 6(b) (mp 162–162.5° C. from acetonitrile). Finally, compound 6(b) was treated with 2-cyanoethyl-N,N,N',N'-tetraisopropylphosphorodiamidite in the presence of 1H-tetrazole to give the phosphoramidite reagent 1(b) in 95% yield. Phosphoramidite 1(b) was isolated by column chromatography on silica gel as a white foam.

EXAMPLE 2

The compatibility of the phosphoramidite 1(a) in oligonucleotide synthesis, as well as the usefulness of the resulting DNA fragments in generation of oligonucleotide 5'-phosphates was studied. In Scheme 2, illustrated below, it was determined that a 5'-terminal phosphate could be coupled with another molecule using a phosphoramidite compound according to the invention.

the 5'-tethered deoxynucleotide into the 5'-phosphate. First, it was found that the product patterns differed significantly depending on whether the oligonucleotide carried a 5'-terminal dimethoxytrityl group when subjected to ammonolysis. The formation of compound 7 was observed only when the solid support 4 was detritylated before the final deprotection. In contrast, when compound 4 having the 5'-OH group still dimethoxytritylated was released and deprotected with either concentrated aqueous ammonia, methylamine, or 1,3-propanediamine (step iii), the conjugate 5 was obtained. Its structure was established as follows: (i) treatment with all three amines gave products that coeluted on an RP column; and (ii) the products obtained by ammonia and methylamine deprotection of compound 4 (10–25 μmol) were shown to exhibit $^1$H NMR signals of thymidine and the non-nucleosidic moiety 3(a). The stability of the ester groups in compound 5 toward ammonolysis and aminolysis

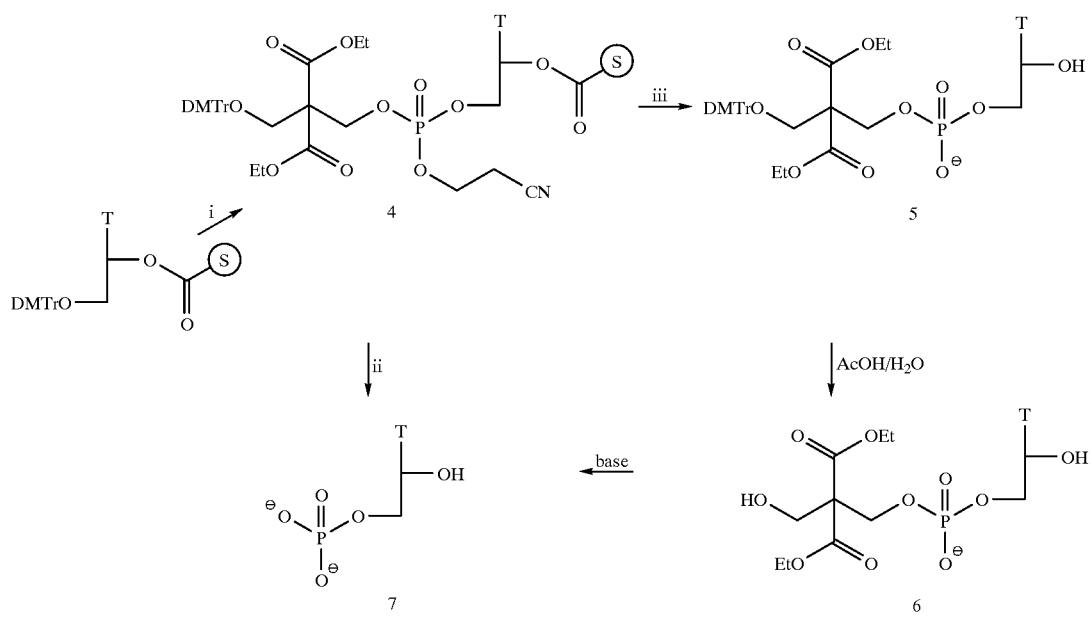

i. a) DCA/CH$_2$Cl$_2$; b) 1(a)/1H-tetrazole; c) I$_2$/Py/H$_2$O/THF; ii: a) DCA/CH$_2$Cl$_2$;
b) NH$_3$H$_2$O; iii: NH$_3$H$_2$O; base:NH$_3$—H$_2$O, MeNH$_2$, 1,3-propanediamine. "S" represents a solid support. "T" represents thymidine.

First, using a standard coupling protocol (step i), commercially available thymidine ("T") derivatized solid support ("S") (0.2 μmol) was detritylated, treated with compound 1(a) (0.1 M in MeCN) and excess 1H-tetrazole, and oxidized with iodine solution to produce compound 4. Measurement of the coupling efficiency by conventional deprotection with 3% dichloroacetic acid ("DCA") in methylene dichloride (step ii (a)) showed that the detritylation reaction was completed in 5 minutes. Coupling yield, however, was found to be satisfactory (99%). Subsequent ammonolysis (step ii (b)) gave a deoxynucleotide derivative which was compared with commercial samples of thymidine and thymidine 5'-phosphate by ion exchange and RP HPLC. According to these comparisons, the reaction mixture consisted of 99% thymidine 5'-phosphate, 7, and 1% thymidine. The ratio of the starting material and product agreed with the result of the dimethoxytrityl assay.

The next question was to clarify which step of the deprotection procedure was responsible for conversion of is rather unexpected and contrasts to the known behavior of the alkyl ester function under similar conditions (see Hovinen et al., *Tetrahedron*, 1994, 50, 7203–7218; and Ramalingam et al., *Tetrahedron*, 1995, 51, 2875–2894, each of which is entirely incorporated herein by reference). Detritylation of compound 5 with 80% aqueous acetic acid ("AcOH") for 30 minutes led to compound 6 in 91% yield, which was characterized by $^1$H and $^{31}$P NMR.

The phosphodiester 6 was found to be stable under neutral conditions. However, when treated with dilute base, it rapidly converted into thymidine 5'-phosphate 7. In order to estimate the half-life of this reaction in the basic media, several experiments were carried out using decreasing concentrations of different aqueous amines: ammonia, methylamine, and n-butylamine. The reaction was too fast to be monitored by RP HPLC in 1.0 and 0.1 M aq. solutions of these amines at ambient temperature (>95% conversion in 15 minutes). In 0.01 M aq. n-butylamine, the half-life was found to be about 15 minutes, and a number of intermediates were detected in the reaction mixture. None of them was accumulated at a marked extent, and the reaction was smoothly completed in 3 hours. Independent of the amine employed, the yield of compound 7 was repeatedly greater than 99.5%.

Alternatively, instead of organic and amine bases, inorganic bases, such as sodium hydroxide (e.g., 0.1 M) can be used to convert phosphodiester 6 to phosphorylated compound 7.

EXAMPLE 3

Synthesis of Oligodeoxynucleotide 5'-phosphates

Because the results of Example 2 appeared to offer a convenient method for the 5'-terminal phosphorylation of oligonucleotides, they were verified by applying the phosphoramidite 1(a) in a DNA synthesis. The overall reaction scheme is illustrated below:

standard protocol was employed (0.1 M compound 1(a) in acetonitrile, coupling time 25 seconds), the coupling yield was found to be greater than 98%. This yield was comparable to that obtained with commercial phosphoramidites.

The deprotection of the anchored oligonucleotide 9 can proceed by two mechanisms, and led generally to the same results observed with compound 4 (Scheme 2). In one reaction mechanism, compound 9 was treated with 3% DCA in methylene dichloride (step ii) to give compound 12, a material having the DMTr group removed. If the synthesis was carried out in this DMTr-Off mode (final detritylation for 5 minutes), the partially protected oligonucleotide 12 underwent conversion to the 5'-phosphorylated derivative 11b during base deprotection (e.g., with aqueous ammonia).

Alternatively, in the other reaction mechanism, ammonolysis of compound 9 led to a stable DMTr-On derivative, 13, which was isolated by RP HPLC to obtain a highly purified product. The RP HPLC profile of compound 13 is shown in FIG. 1.

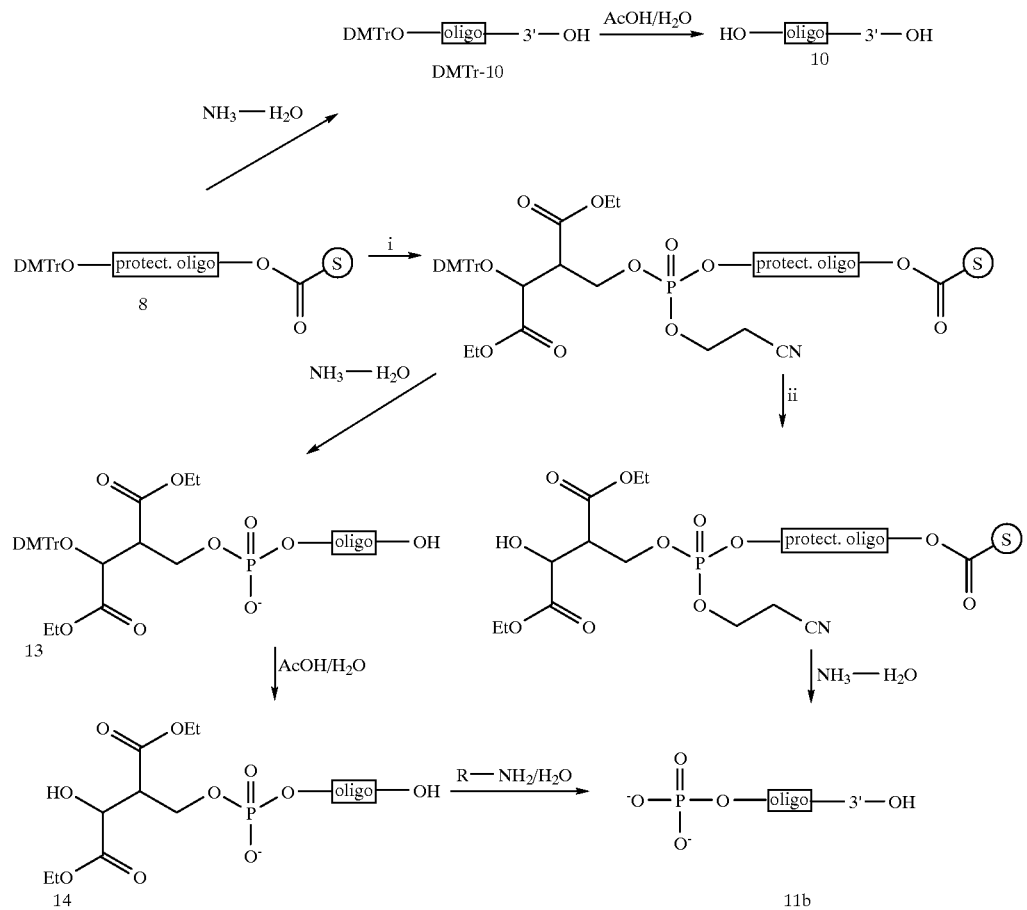

i: a) 1(a)/1H-tetrazole; b) I$_2$H$_2$O/Py/THF; ii: 3% dichloroacetic acid/CH$_2$Cl$_2$.
R is H, CH$_3$, or n-C$_4$H$_9$.

Figure 2:
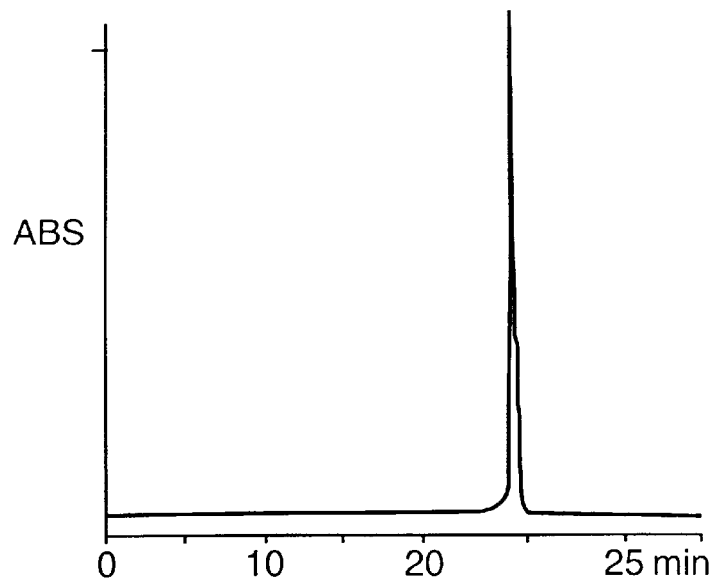
FIG. 2 is an RP HPLC profile of compound 14 in its crude form.

A protected oligonucleotide 5'-GAACATCATGGTCGT-3' (8) (SEQ ID NO:1) was assembled on a commercial solid support by conventional techniques known in the art. The phosphoramidite 1(a) was reacted with compound 8 and attached to its 5'-terminus to give compound 9. When the Detritylation of compound 13 under aqueous conditions does not markedly differ from that of underivatized oligonucleotides. This contrasts to the exceptional resistance of the dimethoxytrityl protected 9 and its analogues toward treatment with dichloroacetic acid in methylene dichloride, as mentioned above. Conventional detritylation (80% aq. AcOH; 20 minutes) converts compound 13 into the corresponding alcohol 14, which was found to be stable under neutral or slightly acidic conditions (pH 5–7) for several days. Oligonucleotide 14 could be rechromatographed by either RP HPLC (as shown in FIG. 2) or ion exchange chromatography. This procedure, however, is not routinely required.

Figure 3:
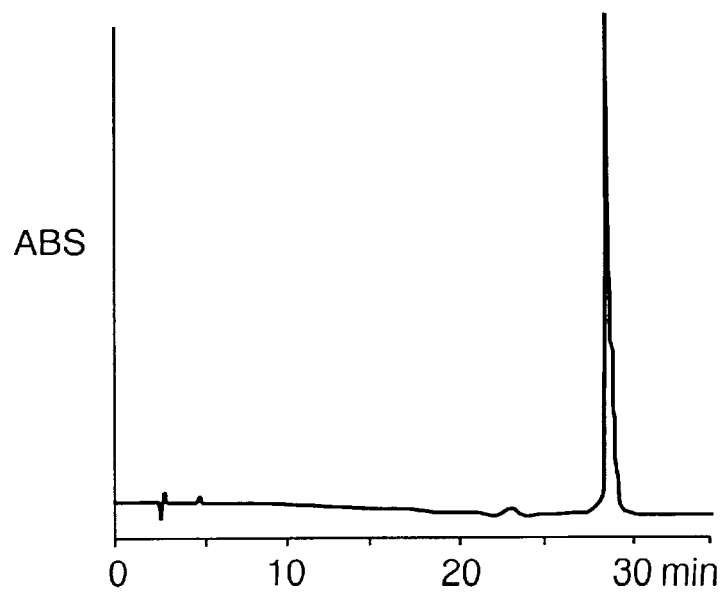
FIG. 3 is an ion exchange profile of compound 11b in its crude form.

When treated with dilute base, compound 14 was rapidly converted into 5'-phosphorylated oligonucleotide 11b. Again, the use of aqueous ammonia, methylamine, or n-butylamine in a concentration higher than 0.1 M led to formation of compound 11b in a yield of 98.5 to 99.5% within 15 minutes. The ion exchange profile of compound 11b is shown in FIG. 3. The reaction mixtures contained 0.5 to 1.5% of an unidentified oligonucleotide of lower negative charge and higher hydrophobicity.

As control samples, non-phosphorylated oligonucleotide (10) and oligonucleotide 5'-phosphate (11a) of the same sequence were prepared to compare their structures against compound 11b. To synthesize compound 11a, the reported method of Horn et al., (*Tetrahedron Letters*, 1986, 27, 4705–4708) using commercial Phosphoralink™ reagent (available from Applied Biosystems, a division of the Perkin Elmer Corp., *User Bulletin*, 1994, 86) was adopted. The Horn article is entirely incorporated herein by reference. Upon conventional deprotection, the crude reaction mixtures were analyzed by ion exchange and/or RP HPLC. The retention times observed are shown in Table 1.

TABLE 1

HPLC Retention Times (in minutes) of the Oligonucleotides Prepared

| Oligo[a] | 5'-DMTr-10 | 10 | 11a[c,d] | 13 | 14 | 11b[d,e] |
|---|---|---|---|---|---|---|
| RP[b] | 26.2 | 21.2 | 20.3 | 25.8 | 22.9 | 20.3 |
| Ion exchange[b] | — | 23.5 | 28.6 | — | 23.5 | 28.6 | a. For the structures, consult Scheme 3.
b. For the conditions, see the Experimental Section.
c. Prepared by the method of Horn, supra.
d. Coeluted when coinjected.
e. Prepared using compound 1(a).

As can be seen from this Table, oligonucleotide 11b, prepared by both routes of deprotection shown in Scheme 3, were found to be identical to the authentic 11a control sample.

Thus, in a routine preparation of oligonucleotide 5'-phosphates, it is more than sufficient to purify and detritylate compound 9, followed by treatment of crude compound 14 with concentrated ammonia for 15 minutes. Upon evaporation of the reaction mixture, the desired product, compound 11b, may be isolated by HPLC.

EXAMPLE 4

Mechanism of the 5'-Terminal Phosphate Deprotection

The conversion of compound 6 to compound 7 and compounds 12 and 14 to 11b proceeds very easily in aqueous amines. No data on the base catalyzed reactions of compound 2(a) or its monoethers has been reported. Applicants' attempts to rationalize the reactivity of compounds 6, 12, and 14 revealed that compounds 2(a) and 3(a) are extremely sensitive to the basic conditions. For example, compound 3(a) disappeared quantitatively within 30 minutes when treated with a catalytic amount of n-butylamine (0.1 eq.) in aqueous pyridine. The only UV-absorbing product detected in the mixture was 4,4'-dimethoxytrityl alcohol (characterized by $^1$H and $^{13}$C NMR). O,O-Alkylidene derivatives of compound 2(a) are, in turn, known to be smoothly hydrolyzed with strong alkali to the corresponding dicarboxylates, the 1,3-dioxane moiety remaining intact (see MacCorquodale et al., *J Chem. Soc. Perkin Trans. II*, 1991, 1893–1899; Hughes et al., *J Am. Chem. Soc.*, 1988, 110, 7494–7499; and Bosies et al., *Lipids*, 1987, 22, 947–951, each of which is entirely incorporated herein by reference). Similarly, dimercapto analogues of compound 2(a) are, in both free and cyclic disulfide form, resistant to treatment with 1,2-ethanediamine (see Teuber et al., *Acta Chemica Scand.*, 1988, B42, 629–634, which article is entirely incorporated herein by reference). These observations illustrate that the presence of a least one unprotected hydroxy group greatly destabilizes the 1,3-propanediol fragment of compound 2(a) and its derivatives.

Mechanistically, the phenomenon could be explained as a two-step process. First, a retrograde aldol reaction of compound 15 that generates an intermediate 16, may occur under basic conditions (see Scheme 4, below) (note, March, *Advanced Organic Chemistry-Reactions, Mechanisms, and Structure*, J. Wiley & Sons, N.Y., 3rd Ed., 1985, 829–834; and Conant, *Org. Syntheses, Coll.* Vol. 1, 199–201, which documents are entirely incorporated herein by reference).

Scheme 4:

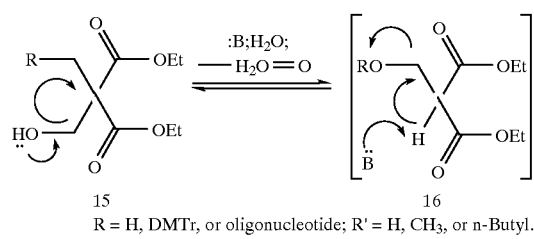
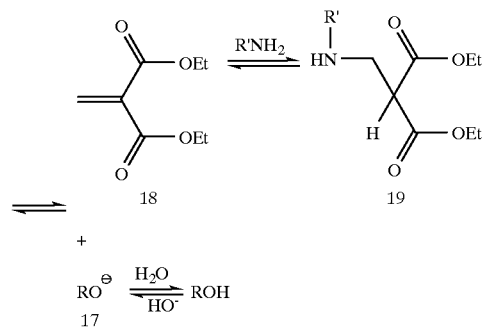

R = H, DMTr, or oligonucleotide; R' = H, CH$_3$, or n-Butyl.

One can expect that, being a reversible reaction, the process should be facilitated by the presence of primary amines or ammonia which are able to trap the released formaldehyde. Compound 16 should, in turn, be extremely susceptible to the elimination reaction leading to compound 17 which, in the present case, is an oligonucleotide 5'-phosphate. The other product then tentatively may be assigned as a diethyl methylenemalonate 18. Finally, the amine might be expected to undergo conjugate nucleophilic 1,4-addition with compound 18 to give compound 19. (See March, *Advanced Organic Chemistry-Reactions, Mechanisms and Structure*, J. Wiley & Sons, N.Y., 3rd Ed., 1985, 689–691; and Casy et al., *J Chem. Soc.* 1964, 4639–4640, which documents are entirely incorporated herein by reference).

EXAMPLE 5

Introduction of 5'-Terminal Phosphate With the Aid of Dimethylamide Phosphoramidite 1(b)

The usefulness of the dimethylamide phosphoramidite reagent 1(b) in producing oligonucleotides that are phosphorylated at their 5'-terminus was verified by on-line phosphorylation of a preassembled synthetic oligonucleotide 20 according to Scheme 5.

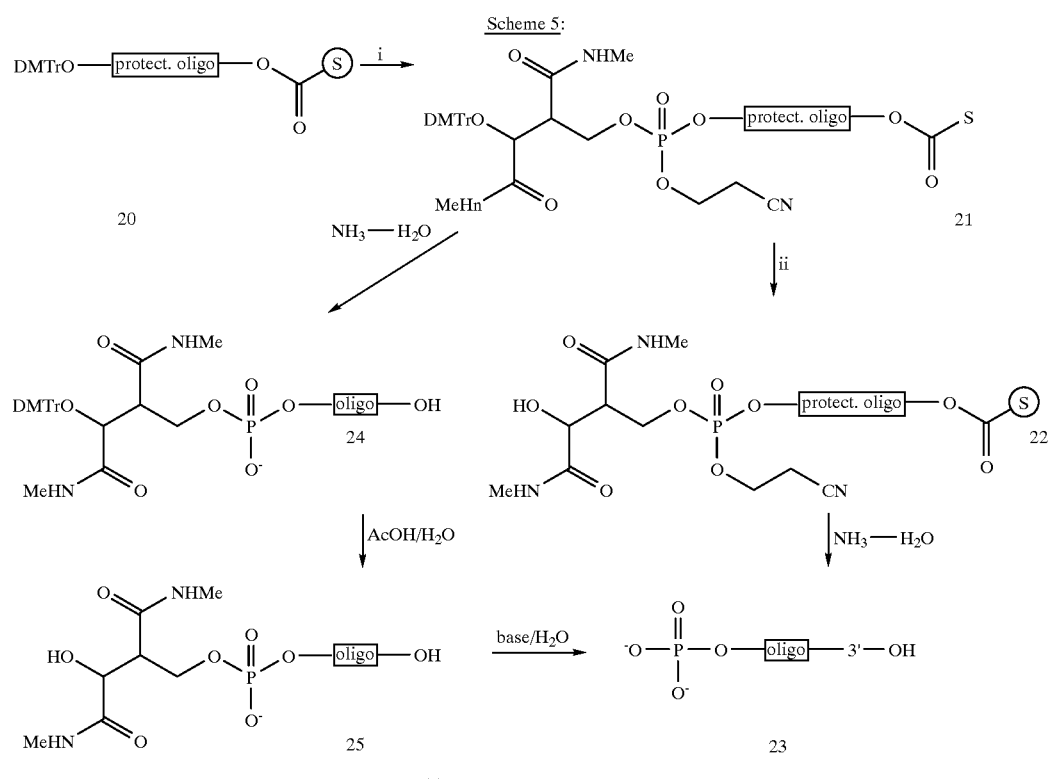

i: DNA condensation step using phosphoramidite 1(b); ii: 3% dichloroacetic acid in methylene dichloride.

The stability of compounds 6, 12, and 14 under acidic conditions is expected: derivatives of compound 2(a) are known to stand weak acids. Yanagawa et al., *Synthesis*, 1973, 607–608; Cassady et al., *Org. Syntheses*, 1983, 61, 77–82; Haynes et al., *Aust. J Chem.*, 1984, 37, 1571–1578; and Singh et al., *J. Am. Chem. Soc.*, 1990, 112, 1190–1197, which articles each are entirely incorporated herein by reference. Only when concentrated solutions of aqueous mineral acids are applied, compound 2(a) undergoes ester bond hydrolysis followed by decarboxylation.

Accordingly, the examples above demonstrate that the non-nucleosidic building block 1(a) allows the efficient preparation of oligonucleotide 5'-phosphates by employing only the procedures and ancillary reagents used in routine DNA synthesis. The precursor of the oligonucleotide 5'-phosphate contains a dimethoxytrityl protecting group and thus can be easily isolated by RP HPLC. Subsequent treatments give rise to the target oligonucleotide 5'-phosphate in a high yield within less than 1 hour.

The support-bound oligonucleotide 20 can be prepared by standard techniques known to those skilled in the art. As a first step in this reaction scheme, the support-bound compound 20 was reacted with compound 1(b) (0.1 M solution in acetonitrile) to produce compound 21. The reagent 1(b) (0.1 M solution in acetonitrile) was found to be stable in the dry acetonitrile solution for at least one week. When it was employed within the standard coupling protocol of the ABI DNA synthesizer (available from Applied Biosystems), coupling yield of compound 21 (more than 98% determined by DMTr-assay) was found to be unaltered in comparison to nucleosidic building blocks. If final cleavage of the DMTr-protecting group from the derivatized oligonucleotide 21 was carried out on the machine, quantitative detritylation can be achieved by using the ABI detritylation protocol for pyrimidine nucleosides.

From compound 21, one of two different reaction mechanisms can be pursued, as shown in Scheme 5 (i.e., the DMTr-On procedure and the DMTr-Off procedure). The obtained results, as will be discussed below, confirmed excellent coupling efficiency of the reagent 1(b) as well as stability of the attached non-nucleosidic moiety in 21 toward ancillary reagents of the DNA synthesis (e.g., capping mixture and oxidizer solution). The structure around the 5'-terminus of the resulting oligonucleotide was found to be dependent on whether the non-nucleosidic moiety was DMTr-protected during ammonolysis. This feature also will be more apparent from the discussion of the reaction procedures that follows.

For the DMTr-Off procedure, the DMTr group on the 5'-derivatized oligonucleotide 21 was removed using 3% DCA in methylene dichloride to produce compound 22. Ammonolysis of the detritylated compound 22 (concentrated aqueous ammonia, 55° C./8 hours) was accompanied with quantitative cleavage of the non-nucleosidic moiety and removal of the solid support S, leading directly to the 5'-phosphorylated oligonucleotide 23.

In contrast, in the DMTr-On procedure, the 5'-derivatized oligonucleotide 21 first was cleaved from its solid support S by ammonolysis using concentrated aqueous ammonia (55° C./8 hours) to produce compound 24. The non-nucleosidic tether remained intact when its pseudo-5' terminal hydroxy group was kept DMTr-protected. This allows one to selectively isolate the modified oligonucleotide 24 by DMTr-specific chromatography, either on an RP HPLC column or manually on an RP-cartridge. After isolation, the DMTr protection on compound 24 can be cleaved under standard conditions (80% aqueous acetic acid, 15 minutes at room temperature), and the product, 25, may, if required, be isolated by either ion exchange or RP HPLC.

In basic media, compound 25 is able to form the 5'-phosphorylated DNA fragment 23. In order to find optimal conditions for the cleavage of the non-nucleosidic tether, oligonucleotide 25 was treated with a variety of organic bases and inorganic alkalis. The following conditions were found to be convenient for routine DNA synthesis:

TABLE 2

Cleavage Reaction Conditions

| ENTRY | CLEAVING AGENT | REACTION TIME (>98% CONVERSION OF COMPOUND 25 INTO COMPOUND 23; ROOM TEMPERATURE) |
|---|---|---|
| 1 | Conc. Aq. NH$_3$ | 6 hours |
| 2 | 1M aqueous MeNH$_2$ | 1 hour |
| 3 | 1M aqueous MeNH$_2$ in Conc. aqueous ammonia | 45 minutes |
| 4 | 1M aqueous NaCl, pH12* | 20 minutes |
| 5 | 0.1M aqueous NaOH, 5 mM ammonium acetate | 10 minutes |

*either adjusted by NaOH or KOH, or 50 mM K$_2$CO$_3$ buffered at pH 12.0.

One can see from this Table that conditions employing either methylamine or ammonia (Entries 1–3) are well suited for the cleavage reaction in the solution since the reagents can be conveniently removed by evaporation. However, the expanding use of RP-cartridges for rapid purification of synthetic oligonucleotides demands somewhat faster reaction rates. This may be achieved by application of inorganic alkalis at high to moderate ionic strength (Entries 4 and 5). The other advantage of these conditions is that high concentration of inorganic salt ensures an efficient stacking of relatively hydrophilic 5'-phosphorylated oligonucleotides to packing material of RP-cartridges that allows nearly quantitive recovery of the target material.

RP cartridge purification can be carried out by the following procedure:

Cartridge Preparation

1. Connect a syringe to the female luer of the cartridge and have the male luer terminate in a waste vessel.
2. Flush the cartridge with 2 mL acetonitrile followed by 2 mL 2 M TEAA (triethylamine acetate, pH 7).

Sample Preparation

3. Following synthesis, deprotect the DMTr-ON oligonucleotide in ammonium hydroxide as normal. For this procedure, there is no need to lyophilize the ammonium hydroxide solution.
4. Add 3 parts deionized water to 1 part of the deprotected DMTr-ON oligonucleotide in the ammonium hydroxide solution. Up to 10 mL of sample solution may result.

Purification Procedure

5. Load the sample solution onto the cartridge. Collect the eluted fraction and again push it through the cartridge. Note: the final eluted fraction may be saved and purified on other Poly-Pak cartridges until all DMTr-ON oligonucleotide is exhausted.
6. Flush the cartridge with 3 mL of ammonium hydroxide (1:20) for oligos<35 mer, or ammonium hydroxide (1:10) for oligos>35 mer.
7. Flush the cartridge with 2 mL of deionized water.
8. Detritylate the support-bound oligonucleotide by flushing the cartridge with 2 mL of 2% TFA (trifluoroacetic acid).
9. Flush the cartridge with 2 mL deionized water.
10. (optional) For oligos>50 mer, repeat steps 6 and 7.
11. Flush the cartridge with 2 mL of cleaving agent. Leave the cleaving agent in contact with the oligonucleotide on the cartridge for 20 minutes at room temperature.
12. Flush the cartridge with 2 mL deionized water.
13. Elute the purified, detritylated oligonucleotide by flushing the cartridge with 20% acetonitrile. Collect the eluted fractions. The first 4 drops of eluent can be discarded and the product is normally in the next 4 to 6 drops.

Alternatively, steps 11 and 12 can be omitted and the cleavage reagent can be added to the oligonucleotide following elution in step 13.

EXPERIMENTAL SECTION

This Experimental Section provides additional details concerning certain reaction schemes and procedures. The information contained in this Section should be construed as illustrating the invention and not as limiting it.

General

Diethyl 2,2-bis (hydroxymethyl)malonate (compounds 2(a) and 2(b)) and 4,4'-dimethoxytrityl chloride (recrystallized before use) were purchased from Aldrich. Reagents (solvents, activators, etc.) for oligonucleotide synthesis were obtained from Cruachem, and {2-[2-(4,4'-dimethoxytrityloxyethyl)sulfonyl]ethyl} (2-cyanoethyl) N,N-diisopropylphosphoramidite was obtained from Applied Biosystems (under the trade name Phosphoralink™). Adsorption column chromatography was performed on Silica gel 60 (available from Merck). NMR spectra were recorded on a Jeol GX-400 spectrometer operating at 399.8 and 161.9 MHz for $^1$H and $^{31}$P, respectively.

Either CDCl$_3$ or DMSO-d$_6$ were used as solvents, with either trimethylsilane ("TMS") as an internal standard ($^1$H) or H$_3$PO$_4$ as an external standard ($^{31}$P).

HPLC Techniques

The oligonucleotides were analyzed and isolated by RP chromatography (column: Nucleosil 300-5C18, 4.0×250 mm, Macherey-Nagel; buffer A: 0.05 M NH$_4$OAc; buffer B: 0.05 M NH$_4$OAc in 65% MeCN, flow rate 1.0 mL min$^{-1}$; a linear gradient from 5 to 60% B in 30 minutes was applied for dimethoxytrityl protected oligonucleotides, otherwise from 0 to 30% B in 30 minutes). Oligonucleotides which did not contain a dimethoxytrityl group were analyzed by ion exchange chromatography (column: SynChropack AX-300, 4.6×250 mm; 6.5 μm, SynChrom, Inc., buffer A: 0.05 M KH$_2$PO$_4$ in 50% formamid; buffer B: A+0.6 M (NH$_4$)$_2$SO$_4$; flow rate 1.0 mL min$^{-1}$; a linear gradient from 25 to 85% B in 35 minutes). Semipreparative RP HPLC was carried out on a Hypersil® ODS column (5 μm; 10×250 mm) by using 0.05 M aq. NaOAc as buffer A, 80% aq. MeCN as buffer B, and water as C at a flow rate of 4.5 mL×min$^{-1}$. Compound 5 was isolated employing a linear gradient from 30 to 90% B in 30 minutes. Desalting was performed on the same column eluted initially with buffer A (10 minutes), then with water (10 minutes). The desalted products were obtained by eluting the column with a mixture of B and C (60:40% for compound 5 and 30:70 for compound 6, correspondingly).

Oligodeoxyribonucleotide Synthesis

The protected oligonucleotides were assembled on an Applied Biosystems 392 DNA Synthesizer using commercial solid support, phosphoramidite chemistry, and recommended protocols for 0.2 and 10 μmol scale. A modified synthetic cycle was used for preparing compound 4 in 25 μmol scale. Accordingly, a mixture of 1H-tetrazole and phosphoramidite solutions was delivered to the column for 34 seconds. All the steps involving the delivery of MeCN, oxidizer, or capping mixture to the column, as well as the reversed flush steps, were reprogrammed for a longer time, as much as twice that employed in the ABI 10 μmol protocol. The detritylation step was carried out by using two consequent "#14 (acid solution) to column" steps (2×80 seconds), separated by a trityl flush step (7 seconds). Phosphoramidite 1(a) was used as a 0.1 M solution in dry MeCN, with unaltered coupling time. The oligonucleotides were deprotected with conc. aqueous NH$_3$ (2 hours at room temperature, then 7 hours at 55° C.), and then analyzed and isolated by HPLC. For 5'-DMTr-10 and compound 13, the dimethoxytrityl group was cleaved with 80% aq. AcOH for 20 minutes at ambient temperature, followed by analysis on both RP and ion exchange columns and RP-isolation of compounds 10 and 14.

5'-Phosphate Deprotection Experiments

Aliquots of purified compound 14 (20 AU/mL; 50 μL) were diluted to 250 μL with an aqueous solution of ammonia or appropriate amine, giving the following final concentrations: ammonia: 25%, 1.0, 0.1 M; methylamine: 1.0, 0.1 M; n-butylamine: 1.0, 0.1, 0.01 M. Samples (50 μL) of the reaction mixtures were taken after 15 and 30 minutes, evaporated to dryness, dissolved in water (250 μL), and analyzed by RP HPLC comparing retention times with those of compounds 14 and 11a. Additional samples (50 μL) were withdrawn from the reaction in 0.01 M aqueous n-butylamine at 60, 120, and 180 minutes. The aliquots were treated and analyzed as described above.

Procedure for Isolation and Final Deprotection of Oligodeoxynucleotide 5'-Phosphates A preassembled oligonucleotide 9 was ammonolyzed to give 13, which, after removal of ammonia by evaporation, was isolated by RP HPLC (see FIG. 1). Dimethoxytrityl protection was cleaved as specified above to produce compound 14, and compound 14 was purified by RP HPLC (see FIG. 2). The fraction collected (cca. 0.4 mL) was diluted with concentrated ammonia (2 mL), left at room temperature for 15 minutes, and evaporated to dryness. The residue was dissolved in water (1 mL), analyzed by ion exchange chromatography (FIG. 3), and passed through an RP column. Pure 11b was collected and found to be homogeneous and chromatographically identical (Table 1) to that of compound 11a prepared by the method reported in the literature (see Horn et al., *Tetrahedron Letters*, 1986, 27, 4705–4708).

Diethyl 2-hydroxymethyl-2-(4,4'-dimethoxytrityloxymethyl)malonate 3(a)

Diethyl 2,2-bis(hydroxymethyl) malonate 2(a) (8.46 g, 38.4 mmol) was dried by co-evaporation with pyridine (3×50 mL) and dissolved in a mixture of dry pyridine (50 mL) and dioxane (50 mL). 4,4'-Dimethoxytrityl chloride (7.80 g, 23 mmol, 0.6 eq.) was added to the stirred solution in small portions within 2 hours. The reaction mixture was stirred for 4 hours, after which the reaction was stopped by adding methanol (0.5 mL). The resulting solution was neutralized with triethylamine (3.6 mL) and evaporated in vacuo to an oil. The residue was dissolved in methylene dichloride (200 mL), washed with water (3×50 mL), dried over Na$_2$SO$_4$, and evaporated to dryness. The crude mixture obtained was separated on a silica gel column (40×150 mm) eluting with a gradient of methanol in CH$_2$Cl$_2$ from 0 to 5%. Collected fractions were evaporated to dryness to give 8.77 g (73%) of pure compound 3(a) as a white foam. $^1$HNMR (δ,ppm): 7.40–7.38 (m, 2H, arom); 7.31–7.18 (m, 7H, arom); 6.84–6.80 (m, 4H, arom); 4.22 (sx, 2H, J$^2_{AB}$=10.7 Hz, J$^3_{H^A Me}$=7.1 Hz, CH$_3$—CH$^A$H$^B$O—C=O), 4.17 (sx, 2H, J$^2_{AB}$=10.7 Hz, J$^3_{H^A Me}$=7.1 Hz, CH$_3$—CH$^A$H$^B$O—C=O), 4.17 (sx, 2H, J$^2_{AB}$=10.7 Hz, J$^3_{H^B Me}$=7.1 Hz, CH$_3$—CH$^A$H$^B$O—C=O); 4.13 (br. s., 2H,—CH$_2$OH); 3.77 (s., 6H, 2xCH$_3$O); 3.63 (s., 2H,—CH$_2$ODMTr); 1.22(tr., 6H, J$^3$=7.1 Hz 2xCH$_3$). IR (λ cm$^{-1}$): 3535 (vOH); 1732 (vC=O); 1251 (vC—O—C); 1608, 1582, 1509 (arom.) Anal. Found: C, 68.73; H, 6.50%. Calcd. for C$_{30}$H$_{34}$O$_8$: C, 68.95; H, 6.56%.

(2-Cyanoethyl) [2,2-bis(ethoxycarbonyl)-3-(4,4'-dimethoxyloxy)propyl-1] N,N-diisopropyl phosphoramidite 1(a)

Alcohol 3(a) (650 mg, 1.25 mmol), pre-dried by co-evaporation with MeCN, and (2-cyanoethyl) N,N,N',N'-tetraisopropylphosphorodiamidite (see Nielsen et al., *Nucleic Acids Res.*, 1987, 3626, which article is entirely incorporated herein by reference) (563 mg, 1.87 mmol) were dissolved in dry MeCN (1.5 mL). 1H-Tetrazole (2.92 mL of 0.45 M solution in dry MeCN; 1.31 mmol) was added, and the mixture was stirred for 20 minutes in dry atmosphere at ambient temperature. Aqueous NaHCO$_3$ (5%; 25 mL) was added, and the mixture was extracted with methylene dichloride (100 mL). Extract was washed with saturated NaCl, dried over Na$_2$SO$_4$, and evaporated to a white foam. The foam was dissolved in toluene (3 mL) and added dropwise to dry hexane (75 mL) at room temperature. To remove solid impurities, the solution was filtered, and the filtrate obtained was kept for 2 hours at —25° C. in a dry atmosphere. The solvent was decanted from the product precipitated as a colorless oil. A fresh portion of hexane (50 mL) was added to the precipitate, the mixture was shaken and left at room temperature to settle down. The solvent was decanted, and the residue was dried in vacuo to give compound 1(a) (850 mg, 94%) as a colorless oil. $^{31}$P NMR(δ, ppm): 148.3. T.l.c. (Kieselgel 60 F$_{254}$, MeOH—CH$_2$Cl$_2$, 1:49) R$_f$ 0.7.

Thymidine 5'-[3-(4,4'-dimethoxytrityloxy)-2,2-di(ethoxycarbonyl)propyl-1]phosphate (5).

Method A. Phosphoramidite 1(a) (1.0 M in MeCN) was coupled to thymidine derivatized controlled pore glass in a 10 μmol scale. After completing the synthesis, the solid supported material 4 was dried and treated with concentrated aq. NH$_3$ for 2 days at room temperature. The liquid phase was evaporated to dryness in vacuo, the residue was dissolved in 30% aq. MeOH, and separated by semipreparative RP HPLC. The fraction containing the product was evaporated to an oil, and the residue was desalted on the same column. The solvent was evaporated, the residue was co-evaporated with MeCN (3×5 mL), and, finally, dried in vacuo, to give 10.2 mg (80%) of compound 5 (sodium salt) as a white powder. $^1$H NMR (DMSO-d$_6$): 7.94, 1H, d.J$^4_{Hme}$=1.0 Hz (H-6); 7.27–7.37, 4H, m.; 7.17–7.24, 5H, m.; 6.92–6.85, 4H, m (arom.); 6.22, 1H, dd., J$^3$=5.8, 7.8 Hz (H=1'); 4.35–4.30, 1H, m., J$^2$=9.8 Hz, J$^3$=2.9 Hz (H-5'); 4.30–4.25, 2H, m. (H-5"and H-3'); 4.01, 4H, q. J$^3$=6.9 Hz, (2xCH$_2$CH$_3$); 3.83, 1H, m. (H-4'); 3.73, 6H, s. (2xCH$_3$O); 3.65, 2H, m. (CH$_2$—O—P); 3.48, 1H, d., J$^2_{AB}$=8.8 Hz (CH$_A$H$_B$—ODMTr); 3.44, 1H, d., J$^2_{AB}$=8.8 Hz (CH$_A$H$_B$—ODMTr); 2.12, 1H, m., and 2.02, 1H, m., J$^2_{2',2''}$=13.2 Hz (H-2' and H-2"); 1.84, 3H, d., J$^4_{MeH}$=1.0 Hz (C$^5$—CH$_3$); 1.06, t., J$^3$=7.1 Hz, and 1.05, t., J$^3$=7.0 Hz, totally 6H, (2xCH$_2$CH$_3$).

Method B. The solid support 4 (25 μmol) was prepared analogously to that in Method A and then treated with 40% aq. methylamine (25 mL) for 2 hours at room temperature. The reaction mixture was worked up, and the product was isolated as described above to give 18.3 mg (86.2%) of compound 5 as a white powder, which was identical to that prepared by Method A as evidenced by $^1$H NMR and analytical RP HPLC.

Method C. Deprotection of the solid support 4 (0.2 μmol) with 50% aq. 1,3-propanediamine (75 μL) for 12 hours at room temperature followed by evaporation of the liquid phase gave the single product, compound 5, which coeluted with an authentic sample prepared by Method A when coinjected on analytical RP HPLC.

Thymidine 5'-[3-hydroxy-2,2-di(ethoxycarbonyl)propyl-1]phosphate (6)

Compound 5 (23.7 mg, 28 μmol) was treated with 80% aq. AcOH (25 mL) for 30 minutes at room temperature. The reaction mixture was evaporated in vacuo, co-evaporated with water (3×5 mL), and partitioned between water (5 mL) and CH$_2$Cl$_2$ (15 mL). The organic layer was discarded, and the aqueous phase was extracted with CH$_2$Cl$_2$ (3×5 mL). At this step, the aqueous phase contained a detritylated product in greater than 97% purity, along with contaminating 4,4'-dimethoxytrityl alcohol. The homogeneous product was isolated by semipreparative RP HPLC within the desalting protocol. Evaporation and final drying in vacuo gave the sodium salt of compound 6 (13.9 mg, 91%) as a white powder. $^1$H NMR (DMSO-d$_6$): 8.31, 1H, s. (NH); 7.81, 1H, d., J$^4_{HMe}$=1.0 Hz,.(H-6); 6.22, 1H, dd., J$^3_{1'2'}$=6.1, J$^3_{1'2'}$=7.8 Hz (H-1'); 4.28, 1H, m. (H-3') 4.19–4.06, m., J$^2$=9.8 Hz, J$^3$=2.9 Hz (H-5', H5"), 4.10, q., J$^3$=7.1 Hz and 4.09 q., J$^3$=7.1 Hz (2xCH$_2$CH$_3$) totally 6H; 3.88, 1H, d., and 3.86, 1H, d., J$^2_{AB}$=12.1 Hz (CH$^A$H$^B$OH); 3.79 1H, m. (H-4'); 3.65, 2H, m. (CH$_2$—O—P); 2.11, 1H, m., and 2.04, 1H, m., J$^2_{2',2''}$=13.3 Hz, J$^3_{2'1'}$=7.8 Hz, J$^3_{2'3'}$=5.5 Hz, J$^3_{2''1'}$=6.1 Hz, J$^3_{2''3'}$=2.7 Hz, (H-2' and H-2"); 1.81, 3H, d., J$^4_{MeH}$=1.0 Hz (C$^5$—CH$_3$); 1.15, t., J$^3$=7.1 Hz, and 1.14, t., J$^3$=7.1 Hz, totally 6H, (2xCH$_2$CH$_3$). $^{31}$P NMR (DMSO-d$_6$): −2.20.

In describing the invention, applicants have stated certain theories, reaction schemes, and mechanisms in an effort to disclose how and why the invention works and the manner in which it works. These theories, schemes, and mechanisms are set forth for informational purposes only. Applicants are not to be bound to any specific chemical or physical mechanisms or theories of operation.

While the invention has been described in terms of various specific preferred embodiments and specific examples, those skilled in the art will recognize that various changes and modifications can be made without departing from the spirit and scope of the invention, as defined in the appended claims.

---

---

We claim:

1. A compound of formula 1:

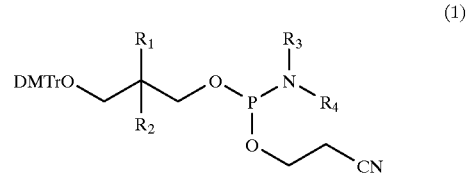

(1)

wherein:

DMTr is a 4,4'-dimethoxytrityl group,

R$_1$ is an electron withdrawing group,

R$_2$ is an electron withdrawing group which may be the same or different from the R$_1$ group, R$_3$ is an alkyl group, and R$_4$ is an alkyl group which may be the same or different from the R$_3$ group.

2. A compound according to claim 1, wherein R$_1$ and R$_2$ each are independently a member selected from the group consisting of an amide group and an ester group.

3. A compound according to claim 1, wherein R$_1$ and R$_2$ each are independently selected from the group consisting of a —CO$_2$Et group, a —CO$_2$Me group, a —CN group, a —CON(Me)$_2$ group, and a —CONHMe group, wherein Et represents an ethyl group and Me represents a methyl group.

4. A compound according to claim 3, wherein at least one of R$_1$ or R$_2$ is a —CO$_2$Et group.

5. A compound according to claim 4, wherein both R$_1$ and R$_2$ are —CO$_2$Et groups.

6. A compound according to claim 3, wherein at least one of R$_1$ or R$_2$ is a —CONHMe group.

7. A compound according to claim 6, wherein both R$_1$ and R$_2$ are —CONHMe groups.

8. A compound according to claim 3, wherein at least one of R$_1$ or R$_2$ is a —CON(Me)$_2$ group.

9. A compound according to claim 8, wherein both R$_1$ and R$_2$ are —CON(Me)$_2$ groups.

10. A compound according to claim 1, wherein at least one of R$_3$ or R$_4$ is an isopropyl group.

11. A compound according to claim 10, wherein both R$_3$ and R$_4$ are isopropyl groups.

12. A compound according to claim 4, wherein at least one of R$_3$ or R$_4$ is an isopropyl group.

13. A compound according to claim 6, wherein at least one of R$_3$ or R$_4$ is an isopropyl group.

14. A compound according to claim 8, wherein at least one of R$_3$ or R$_4$ is an isopropyl group.

15. A compound according to claim 1 having the following formula:

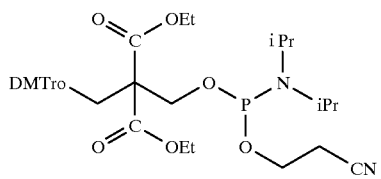

wherein Et is an ethyl group and iPr is an isopropyl group.

16. A compound according to claim 1 having the following formula:

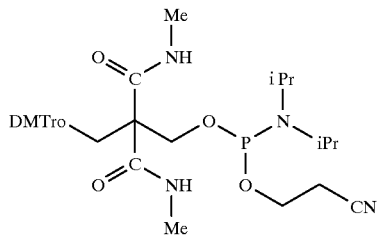

wherein Me is a methyl group and iPr is an isopropyl group.

17. A compound according to claim 1 having the following formula:

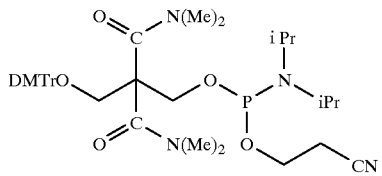

wherein Me is a methyl group and iPr is an isopropyl group.

18. A process for phosphorylating an oligonucleotide, comprising:
reacting a support-bound 4,4'-dimethoxytrityl protected oligonucleotide of the formula:

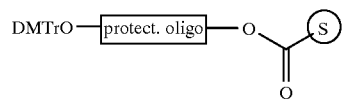

wherein DMTr is a 4,4'-dimethoxytrityl group, and S is a support material, with a phosphoramidite of formula 1:

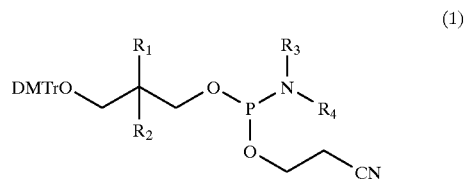

wherein:

DMTr is a 4,4'-dimethoxytrityl group,

R$_1$ is an electron withdrawing group,

R$_2$ is an electron withdrawing group which may be the same or different from the R$_1$ group, R$_3$ is an alkyl group, and R$_4$ is an alkyl group which may be the same or different from the R$_3$ group, to form a phosphorylated oligonucleotide of the formula:

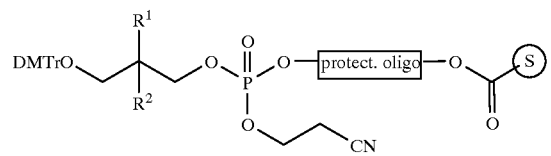

cleaving the phosphorylated oligonucleotide from the support material to provide an unbound phosphorylated oligonucleotide of the formula:

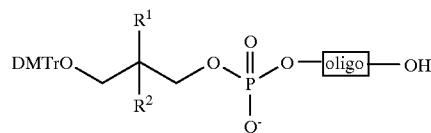

recovering the unbound phosphorylated oligonucleotide;

removing the DMTrO group from the phosphorylated oligonucleotide to form a phosphorylated oligonucleotide of the formula:

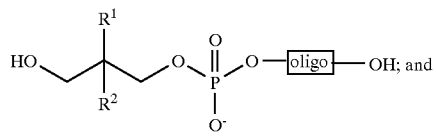

removing the

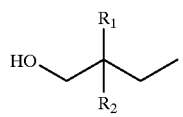

side chain on the phosphorylated oligonucleotide to provide an oligonucleotide having a phosphate group of the formula:

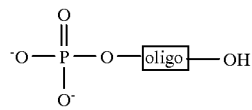

19. A process according to claim 18, wherein the unbound phosphorylated oligonucleotide is recovered by a reverse phase separation technique.

20. A process according to claim 18, wherein $R_1$ and $R_2$ each are independently a member selected from the group consisting of an amide group and an ester group.

21. A process according to claim 18, wherein $R_1$ and $R_2$ each are independently selected from the group consisting of a —$CO_2Et$ group, a —$CO_2Me$ group, a —CN group, a —$CON(Me)_2$ group, and a —CONHMe group, wherein Et represents an ethyl group and Me represents a methyl group.

22. A process according to claim 21, wherein at least one of $R_1$ or $R_2$ is a —$CO_2Et$ group.

23. A process according to claim 22, wherein both $R_1$ and $R_2$ are —$CO_2Et$ groups.

24. A process according to claim 21, wherein at least one of $R_1$ or $R_2$ is a —CONHMe group.

25. A process according to claim 24, wherein both $R_1$ and $R_2$ are —CONHMe groups.

26. A process according to claim 21, wherein at least one of $R_1$ or $R_2$ is a —$CON(Me)_2$ group.

27. A process according to claim 26, wherein both $R_1$ and $R_2$ are —$CON(Me)_2$ groups.

28. A process according to claim 18, wherein at least one of $R_3$ or $R_4$ is an isopropyl group.

29. A process according to claim 28, wherein both $R_3$ and $R_4$ are isopropyl groups.

30. A process according to claim 22, wherein at least one of $R_3$ or $R_4$ is an isopropyl group.

31. A process according to claim 24, wherein at least one of $R_3$ or $R_4$ is an isopropyl group.

32. A process according to claim 26, wherein at least one of $R_3$ or $R_4$ is an isopropyl group.

33. A process according to claim 18, wherein the phosphoramidite according to formula 1 is the following compound:

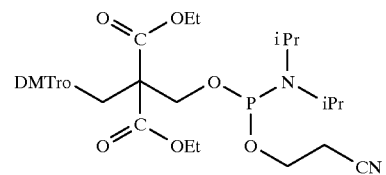

wherein Et is an ethyl group and iPr is an isopropyl group.

34. A process according to claim 18, wherein the phosphoramidite according to formula 1 is the following compound:

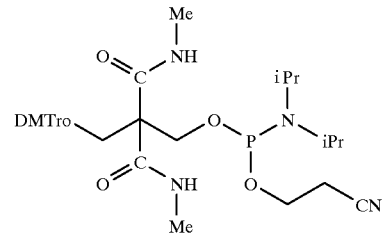

wherein Me is a methyl group and iPr is an isopropyl group.

35. A process according to claim 18, wherein the phosphoramidite according to formula 1 is the following compound:

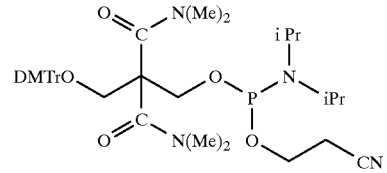

wherein Me is a methyl group and iPr is an isopropyl group.

36. A process according to claim 18, wherein the support material is a member selected from the group consisting of silica, controlled pore glass, long chain alkyl amino controlled pore glass, and polystyrene.

37. A process according to claim 18, wherein the oligonucleotide includes a nucleotide chain having from about 2 to about 200 component nucleotide monomers.

38. A process according to claim 18, wherein the oligonucleotide product is an oligonucleotide having a phosphate group at the 5'-terminus.

39. A process according to claim 38, wherein the oligonucleotide product produced is substantially pure.

40. A process according to claim 18, wherein the oligonucleotide product is of the formula:

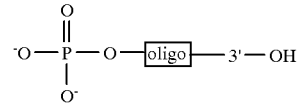

* * * * *